United States Patent [19]
Geiger et al.

[11] Patent Number: 5,589,342
[45] Date of Patent: Dec. 31, 1996

[54] KIT FOR SEPARATING DOUBLE-STRANDED NUCLEIC ACID FROM A SINGLE-STRANDED/DOUBLE-STRANDED MIXTURE OF NUCLEIC ACIDS

[75] Inventors: Jon R. Geiger, West Hartford; Samuel I. Trotz, Orange, both of Conn.

[73] Assignee: Olin Corporation, Cheshire, Conn.

[21] Appl. No.: 615,095

[22] Filed: Nov. 19, 1990

Related U.S. Application Data

[62] Division of Ser. No. 944,919, Dec. 22, 1986, Pat. No. 5,034,314.

[51] Int. Cl.$^6$ ............................................. C12Q 1/68
[52] U.S. Cl. ........................ 435/6; 422/68.1; 422/69; 435/803; 435/810; 435/287.2; 436/501; 436/17; 536/24.3; 536/24.31; 536/24.32; 536/25.4; 935/77; 935/78
[58] Field of Search ............................ 435/6, 311, 803, 435/291, 810; 436/17, 501; 536/27, 24.3–24.32, 25.4; 935/9, 19, 85, 77, 78; 422/68.1, 69

[56] References Cited

U.S. PATENT DOCUMENTS

| | | | |
|---|---|---|---|
| 4,599,303 | 7/1986 | Yabusaki et al. | 435/6 |
| 4,623,723 | 11/1986 | Keller et al. | 536/27 |
| 4,727,019 | 2/1988 | Valkirs et al. | 435/5 |

FOREIGN PATENT DOCUMENTS

| | | |
|---|---|---|
| 0070685 | 1/1983 | European Pat. Off. . |
| 0070687 | 1/1983 | European Pat. Off. . |

*Primary Examiner*—W. Gary Jones
*Assistant Examiner*—Ardin H. Marschel
*Attorney, Agent, or Firm*—Dale L. Carlson

[57] ABSTRACT

A method and a kit for separating double-stranded nucleic acid molecules from a mixture containing both single-stranded and double-stranded nucleic acid molecules. The method is particularly suitable for separating hybridized from unhybridized probe nucleic acid.

2 Claims, No Drawings

KIT FOR SEPARATING DOUBLE-STRANDED NUCLEIC ACID FROM A SINGLE-STRANDED/DOUBLE-STRANDED MIXTURE OF NUCLEIC ACIDS

This application is a division of application Ser. No. 944,919 filed Dec. 22, 1986 now U.S. Pat. No. 5,034,314.

BACKGROUND OF THE INVENTION

1. Field of the Invention

This invention relates generally to a method and a kit for separating double-stranded nucleic acid molecules from a mixture containing both single-stranded and double-stranded nucleic acid molecules and is particularly suitable for separating hybridized from unhybridized probe nucleic acids.

2. Description of the Prior Art

An important tool in the rapidly-evolving fields of genetic engineering, environmental microbial contamination monitoring, and medical diagnostics is the use of DNA and RNA probes. DNA and RNA probes are single-stranded nucleic acid molecules generally synthesized by so-called gene machines or made using recombinant DNA methods. Probes are constructed so that the base (i.e., gene) sequences of the probe match (and lend themselves to hybridization with) complementary sequences on a target molecule. They are used for clinical diagnosis of genetic disorders, cancer, and disease-causing bacteria, protozoans, and viruses. In the environmental field, they can be used to rapidly identify specific microbial contaminants. Research scientists use probes in recombinant DNA experiments and in gene activation studies.

Prior to use, each molecule of the probe is labelled with a marker, such as a radioactive tag, in order to allow determination of when and where hybridization has occurred.

Before the hybridized target nucleic acid molecules can be identified based upon the presence of the labelled probe, the unhybridized single-stranded labelled probe molecules must be separated out. Otherwise, this latter material will act as "background noise" inhibiting attempts to identify the hybridized material. Conventionally utilized commercial methods for effecting this separation of hybridized probe molecules from unhybridized single-stranded probe molecules usually involve irammobilizing the target nucleic acid on a membrane which is reactive with nucleic acids. Such membranes bind all nucleic acids nonselectively. In view of this nonselectivity characteristic, the active sites on the membrane must be blocked before probe nucleic acid is added. This blocking entails numerous steps and an incubation period typically of two hours. Thus, the membrane must be treated with various blocking agents after the target DNA is affixed to prevent nonspecific adhesion of the probe nucleic acid so that washing the membrane after hybridization will remove unhybridized probe. Alternatively, selective absorption of double-stranded nucleic acids using hydroxylapatite is employed. The hydroxylapatite serves to effectively separate double-from single-stranded DNA. This capability results from hydroxylapatite's selective affinity for place in a single phase. Commercial kits using conditions.

Either radioactive or nonradioactive probes may be used with the membrane immobilization technique. In a nutshell, the radioactive probe method first involves incubating a membrane, that has single-stranded target sequences attached, with a radioactively labelled probe (usually phosphorus-32 ($^{32}P$)) consisting of a single strand of DNA or RNA with base sequences that are possibly complementary to the target sequences being studied. The probe hybridizes with only those target nucleic acids containing a complementary nucleic acid sequence. After hybridization, the membrane is washed and hybrids are detected by autoradiography. The presence of characteristic hybrid nucleic acid on the autoradiogram is indicative of the presence of a specific target sequence. Typically, the assay of a hybridized radioactively labelled probe requires numerous steps and 40 hours. The extensive time and effort result from the necessity of binding target nucleic acid to the membrane, blocking the remaining sites on the membrane that would otherwise nonspecifically bind labelled probe, hybridizing for long periods of time because the hybridization reaction is a two-phase reaction, and washing numerous times to remove unhybridized probe. Developing the autoradiogram typically takes 24 hours.

Hybridized probe may also be separated from unhybridized probe using hydroxylapatite and appropriate ionic strength buffers (Kohne, D. E., 1984, Patent Cooperation Treaty WO 84/02721). This method, which has only been demonstrated with radioactive probes, is much faster. There is no binding of target DNA to an immobilization support, no blocking of binding sites on a support, fewer washes, and hybridization is more rapid since the reaction take place in a single phase. Commercial kits using hydroxylapatite require only 14 steps and 1.5 hours.

The radioactive method has not been well received in medical diagnostics laboratories for several reasons. First, the high specific activity radioactive materials typically used in kits employing this method have a relatively short half life. Consequently, the complementary probe DNA must be prepared just prior to the hybridization procedure. Secondly, the radioactive material creates more rigid handling problems and undesirable hazards. It is therefore advantageous in most cases to provide a label which is less hazardous and prolongs the shelf life of the probe.

The development of non-radioactive labelling of nucleic acid probes presents an alternative. A typical non-radioactive system is based on the incorporation of a biotinylated deoxyuridine triphosphate into the DNA probe by the nick translation procedure. The resultant biotinylated DNA probe is stable and behaves as does a non-biotinylated DNA probe. The biotinylated DNA probe technique has been applied to the detection of specific DNA and RNA sequences in fixed cells or in tissues following in situ hybridizations. It has also been used to visualize probe nucleic acid hybridized to target nucleic acid immobilized on membranes. The detection of the hybridized biotinylated probe is accomplished by either fluorescent antibody or enzyme amplification techniques. A typical non-radioactive labelled probe assay such as an enzyme labelled probe method using membrane-bound target DNA generally requires at least 32 steps and 18 hours. More washes are required than in the case where a radioactive probe is used, but development of the signal is more rapid. Thus, although avoiding the problems of radioactivity, the conventional enzyme-label method is cumbersome in view of the large number of steps and the long test time generally attributable to the above-described immobilization of target nucleic acid on a membrane as the method to effect separation of hybridized from unhybridized probe nucleic acid.

A number of suggestions have been made in the literature for alternative separation methods to recover the hybridized probe target molecules. For example, U.S. Pat. No. 4,599, 303, which teaches a method of first hybridizing and then forming covalent bonds between probe and target, discloses at column 2, lines 55–61 thereof, several procedures for separating covalently crosslinked double-stranded probe-target complex from single-stranded probe. These procedures are described as including gel filtration, hydroxylapatite chromatography, enzymatic digestion, alkaline hydrolysis, and photoreversal or chemical reversal of uncrosslinked crosslinking molecules.

The gel filtration technique referred to in the '303 patent generally denotes a column chromatography-type procedure whereby large molecules in the assay mixture pass through channels in the gel, whereas the smaller molecules elute at different velocities through the gel to effect a separation. This gel filtration procedure is believed by the present inventors to be slow, cumbersome, and subject to failure since, with sufficient elution, the entire assay mixture will pass through the column.

In view of the above, new methods for separating single-stranded probe nucleic acid from double-stranded probe target nucleic acid molecules are expected to be highly desired in a commercial setting, particularly in the medical diagnostics and environmental monitoring fields. More specifically, the development of a simpler such technique employable with either radioactive or non-radioactive labelled probes for clinical diagnosis and environmental monitoring would undoubtedly enhance this technique and will have a competitive advantage relative to current approaches.

SUMMARY OF THE INVENTION

In one aspect, the present invention relates to a method for separating double-stranded nucleic acid molecules from single-stranded nucleic acid molecules which comprises ultrafiltration of a liquid mixture containing said double-stranded nucleic acid molecules and said single-stranded nucleic acid molecules through an ultrafiltration membrane having a pore size within a range sufficient to pass said single-stranded nucleic acid molecules but to retain said double-stranded molecules on said filter. As used herein, the terms "ultrafiltration" and "ultrafiltering" denote filtration using a membrane filter having a sufficiently small pore size such that macromolecules of a particular molecular weight, typically from 50,000 to 1,000,000 daltons, are retained by the filter.

In another aspect, the present invention relates to a method for determining the presence of specific nucleic acid base sequences in single-stranded nucleic acid target molecules comprising the steps of:

(a) providing single-stranded labelled nucleic acid probe molecules having an essentially complementary base sequence to a defined region in the single-stranded target molecules;

(b) hybridizing at least a portion of said single-stranded labelled nucleic acid probe molecules to said defined region in at least a portion of said target molecules, thereby forming a mixture of hybridized molecules and single-stranded molecules;

(c) ultrafiltering said mixture using a membrane filter having a molecular weight cutoff sufficient to pass said portion of said single-stranded labelled nucleic acid probe molecules through said filter but retain said hybridized molecules on said filter; and (d) measuring the amount of said portion of said single-stranded labelled nucleic acid probe molecules in said hybridized molecules or the amount of single-stranded labelled probe molecules that pass through said membrane filter and did not hybridize with target nucleic acid molecules.

In still another aspect, the present invention relates to a kit for effecting separation of labelled probe nucleic acid molecules from hybridized probe/target nucleic acid molecules comprising:

a) a sample of labelled probe nucleic acid molecules and (b) a membrane filter having a pore size within a range such that unhybridized labelled probe nucleic acid molecules pass through said membrane filter whereas labelled probe nucleic acid molecules hybridized with compatible target nucleic acid molecules are retained on said membrane filter.

These and other aspects of the invention will be readily apparent upon reading the detailed description which follows.

DETAILED DESCRIPTION OF THE INVENTION

The target DNA or RNA whose specific base, a portion of whose sequence is generally known, is referred to herein as a target. The polynucleotide containing the label and expected to have a base sequence complementary to the target is referred to herein as a probe. The joining together of both target and complementary probe polynucleotide by the mechanism of base pairing through hydrogen bonds between purine and pyrimidine bases is referred to herein as hybridization and the resultant complex is termed a hybridized nucleic acid molecule or hybridized probe/target molecule.

The nucleic acid probe will consist of chemically synthesized or biologically prepared DNA or RNA polynucleotides from 10 to 2000 bases in length or longer single-stranded sequences including messenger RNAs and single-stranded DNA or RNA. If synthesized, the single-stranded DNA or RNA probe is fabricated so that its nucleic acid base sequence is complementary to a region of the bacterial, vital, or mammalian chromosome target sequence.

Alternatively, probe DNA or RNA can be isolated from biological sources and subsequently reacted with a labelling reagent of interest. Single-stranded DNA can be obtained directly from single-stranded viral genomes such as M13 or ΦX174 or indirectly from double-stranded genomes or plasmids by strand separation. The size of such a probe will be controlled by enzymatic processing including exonuclease treatment of single-stranded DNA and restriction or Bal 31 digestion of double-stranded DNA. In another alternative, the DNA probe can also be prepared enzymatically from appropriate nucleic acid substrates. For example, DNA could be obtained from mRNA using reverse transcriptase. RNA probes can be directly obtained from biological sources in the form of viral genomes (R17, F2, QB) or mRNA. Alternatively, the RNA can be enzymatically synthesized in vitro from appropriate templates. For example, phage RNA polymerase catalyzed transcription of a double-stranded DNA template such as a sequence cloned next to a phage promoter in an appropriate cloning vector would generate probe RNA.

The probe will normally have at least 25 bases, more usually at least several hundred bases, and may have up to about 10,000 bases or more, usually having not more than about 5,000 bases. The probe sequence will be at least substantially complementary to a sequence characteristic of the organism or gene of interest. The probe need not have perfect complementarity to the sequence to which it hybridizes; there may be 30 percent or more of mismatched pairs.

The probe may be obtained from messenger RNA, from ribosomal RNA, or from cDNA obtained by reverse transcription of messenger RNA or ribosomal RNA with reverse trancriptase. Probe may also be obtained by cleavage of the genome, conveniently by endonuclease digestion, followed by cloning of the gene or gene fragment in accordance with known techniques. See, for example, Kornberg, DNA Replication, W. H. Freemen and Co., San Francisco, 1980, pp 670–679; So et al, Infect. Immun. 21:405–411, 1978. After isolation and characterization of the desired gene or DNA fragment, the gene or DNA fragment may be used for preparation of the probe or transcribed for production of RNA, which may then be used for preparation of the probe.

For the most part, the polynucleotide probe will be labelled with an atom or inorganic radical, most commonly using radionuclides, but also perhaps heavy metals. However, in some situations it may be feasible to employ an antibody which will bind specifically to the probe hybridized to the single-stranded target DNA. In this instance, the antibody would be labelled to allow for detection. The same types of labels which are used for the probe may also be bound to the antibody in accordance with known techniques.

If desired, a radioactive label may be employed Radioactive labels include $^{32}P$, $^{3}H$, $^{125}I$, $^{35}S$, $^{14}C$, or the like. Any radioactive label may be employed which provides for an adequate signal and has sufficient half life. Other labels include ligands, which can serve as a specific binding member to a labelled antibody or to a specific binding protein, fluorescers, chemiluminescers, enzymes, antibodies which can serve as a specific binding site for a labelled ligand, and the like. A wide variety of labels have been employed in immunoassays which can readily be employed in the present assay. The choice of the label will be governed by the effect of the label on the rate of hybridization and binding of the probe to the target DNA. It will be necessary that the label provide sufficient sensitivity to detect the amount of DNA available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an alpha-$^{32}P$-dNTP or terminal phosphate hydrolysis with alkaline phospbatase followed by labelling with radioactive $^{32}P$ employing gamma-$^{32}P$-NTP and T4 polynucleotide kinase. Alternatively, nucleotides can be synthesized where one or more of the elements present are replaced with a radioactive isotope, e.g., hydrogen with tritium. If desired, extensions of the probe strand with a simple repetition of one nucleotide (and therefore unlikely to be complementary to any target sequence) can be used to enhance the concentration of hybridized label.

Where other radioactive compounds are involved, various linking groups can be employed. A terminal hydroxyl can be esterified with inorganic acids, e.g., $^{32}P$ phosphate, or $^{14}C$ organic acids, or else esterified to provide linking groups to the label. Alternatively, intermediate bases may be substituted with activatable linking groups which can then be linked to a label.

Ligands and antiligands may be varied widely. Where a ligand has a natural receptor, namely ligands such as biotin, thyroxine, and cortisol, these ligands can be used in conjunction with labelled naturally occurring receptors. Alternatively, any compound can be used, either haptenic or antigenic, in combination with an antibody.

Enzymes of interest as labels will primarily be hydrolases, particularly esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinedioners, e.g., luminol.

The amount of labelled probe which is present in the hybridization solution will vary widely, depending upon the nature of the label, and the stringency of the hybridization. Generally, substantial excesses over a stoichiometric amount of the probe will be employed to enhance the rate of hybridization and to allow the quantifying of the amount of target sequences present.

In the hybridization, the nucleic acid, for example, from a blood, tissue, cell sample, or microorganism from an environmental sample is reacted with the probe under conditions where hybridization of the probe with the target will occur. The probe contains a label molecule which can be a radioactive nuclide, chromogenic, fluorogenic, luminescent dye molecule, magnetic particle, or an enzyme system capable of generating a chromogenic, fluorogenic, and/or luminescent product via appropriate substrates.

The particular hybridization technique employed is not a critical element of the present invention. Various hybridization solutions may be employed, comprising from about 20 to 60, preferably 40 to 50, volume percent of an inert polar organic solvent. A common hybridization solution employs about 50 percent formamide, about 0.05 to 0.5M sodium phosphate, and minor amounts of EDTA. Other additives may also be included, such as dextran sulfate of from about 100 to 1,000 dal and in an amount of from about 8 to 15 weight percent of the hybridization solution. Alternatively, aqueous solutions containing these salts and polymers and free of organic solvents such as formamide may be employed. The hybridization time employed can be one-half hour or less up to several hours or more as desired.

The more stringent these conditions, the greater the complementarity that is required for hybridization between the probe and the target nucleic acid.

The extent of hybridization is affected by various factors, including temperature, probe concentration, probe length, ionic strength, time, and the like. As an illustrative example, the extent of hybridization can be varied by changing the polarity of the reactant solution by manipulating the concentration of formamide in the range of 0 to 50 percent. Alternatively, temperatures can be varied in the range of about 20° to 85° C., usually 30° to 75° C. Generally, atmospheric pressure is employed.

Detection of the hybridized probe will normally be accomplished by measuring the amount of the label on the double-stranded molecule after hybridization. Various methods or protocols may be employed in measuring the amount of the labels on the hybridized probe/target molecules. These protocols include, for example, autoradiography, detection of radioactive decay in a scintillation counter or using a geiger counter, chemiluminescent assays, bioluminescent assays, and assays of enzymes linked either directly or indirectly to the probe, among others.

The hybridized labelled probe/target is separated from unhybridized labelled probe by ultrafiltration. This ultrafiltration is preferably conducted while centrifuging the mixture containing hybridized probe/target, thereby expediting the ultrafiltration process. Ultrafiltration is suitably effected using a membrane filter constructed of any solid network material such as, for example, cellulosic, acrylic, or other material that will not bind either nucleic acid or protein nonspecifically. Centrifugation, if used as a driving force for the ultrafiltration, is generally applied at 1000 to 3000 rpms at between 500 and 2000 RCF (relative centrifugal force), e.g. in a fixed-angle centrifuge rotor.

Alternatively, more conventional ultrafiltration using pressure-driven membrane separation can be employed with pressures between 5 and 20 atmospheres.

The discovery by virtue of the present invention that ultrafiltration on a membrane filter can be used to separate single-stranded (e.g., unhybridized) from double-stranded (e.g., hybridized) nucleic acids is particularly surprising in view of the similar structural configuration of these moieties. Without wishing to be bound by any particular theory, both single-stranded and double-stranded nucleic acids are commonly believed to be linear polymers or to have, at most, some secondary structure, albeit often transitory. They are not globular in configuration like undenaturated proteins. In fact, it is more likely that single-stranded nucleic acid, particularly RNA, has more secondary structure than double-stranded material. This is due to internal homologies in single-stranded material that causes intra-stranded base-pairing with resultant double-stranded regions and interspersed loops of unpaired sections. It was of considerable surprise, therefore, to discover that ultrafiltration could be used to separate bound from unbound probes since ultrafilters, although fabricated and calibrated on the basis of the molecular weight of globular proteins retained, actually separate on the basis of the configuration of the molecules. Our discovery is as unexpected as finding that a spaghetti colander would pass certain forms (and retain slightly wider forms) of pasta, even though the colander's holes in both cases are much bigger than the diameter of both forms of pasta.

Ultrafiltration membranes having a molecular weight cutoff (MWCO) within a range of between about 50,000 and about 1,000,000 daltons are generally useful within the scope of the present invention. An optimal cutoff range is dependent upon the size of the specific probe and target nucleic acids selected. For example, small probes with radioactive signals are expected to have a preferred MWCO of about 100,000 or lower, whereas the preferred MWCO for probes with an enzyme label is between about 100,000 and about 500,000, more preferably between about 200,000 and about 300,000 daltons.

Preferred materials for membrane construction for filters useful in the present invention are those which are hydrophilic and have low nonspecific binding of proteins or nucleic acids. Membranes fabricated of acrylic, cellulosic, or regenerated cellulose compositions are most preferred. Membranes fabricated of aromatic amides or polysulfones are also expected to be useful within the scope of the present invention. Suitable commercially available ultrafiltration membranes can be obtained from Amicon Corporation, Micro Filtration Systems, Schleicher and Schuell, Ultra-Pore Inc., and Millipore Corporation.

Normally, the hybridization and subsequent ultrafiltration steps for isolation of the hybridized labelled probe/target molecules are done in solution without the need for electrophoretic gel separations or blotting procedures. The simplicity of the required manipulations, high sensitivity, and low background of the procedure have clear advantage to other hybridization and isolation assays.

The present invention provides a simple diagnostic method for detection of the pathogenic origin of disease, for detection of genetic anomalies, and for monitoring for microbial contamination. The method finds particular application in infectious and/or genetic disease diagnosis, epidemiology, and water and food monitoring. The method is reasonably rapid, taking about three hours, has a simple protocol, as few as sixteen steps, has reagents which can be standardized and provided in commercial kits, and allows for rapid screening of a large number of samples. In practice, samples can be taken through part of the protocol in "the field" and conveniently returned to a distant laboratory for final completion of the diagnosis.

In carrying out the method of the present invention, a sample suspected of containing the microbe may be used directly or cultivated under conditions where organism growth provides high multiplication of the organism's nucleic acids. A tissue sample suspected of having anomalous gene activity would be used directly. After treating the target to provide single-stranded genomic nucleic acid, the single-stranded DNA or RNA is hybridized with a labelled probe polynucleotide having a complementary base sequence. This hybridization generally takes place in the presence of an excess of probe relative to the amount of the known-sequence target to be hybridized. For example, a 100 fold to 1,000 fold excess of probe to specific target sequences will allow rapid hybridization of all target sequences. Such an excess also allows quantitative analysis of numbers of contaminating organisms in single test.

As stated above, the minimum number of components of a kit in accordance with the present invention is a sample of labelled probe and a membrane filter. However, it is preferred that the kit also contain a suitable lysing system for lysing of cells or viruses to provide the labelled probe nucleic acid molecules for hybridization with the labelled probe nucleic acid molecules. The kit also preferably contains a wash solution (e.g., a phophate-buffered 50 percent formamide solution) for washing unhybridized labelled probe nucleic acid through the membrane filter. If the probe is enzyme labelled, the kit also preferably contains an enzyme substrate and buffer solution to optimize the enzyme's catalytic activity and to allow signal development and/or enhancement of the label for identification of the hybridized probe/target nucleic acid molecules.

Microorganisms which may be detected and identified include bacteria, viruses, fungi, protozoa, algae, etc. Among microorganisms are bacteria, such as gram negative bacilli, e.g. Escherichia, Vibrio, Yersinia, Klebsiella, and Salmonella. Species include *E. coli, Vibrio cholerae, Haemophilus ducrei, Legionella pneumophila*. Other microorganisms of interest are those difficult to cultivate such as the HIV virus, genital Herpes virus, Norwalk Agent virus, Rotavirus, and Giardia.

The following examples are intended to illustrate, but in no way limit, the scope of the present invention.

EXAMPLE 1

HYBRIDIZATION OF PROBE DNA WITH VARIOUS BACTERIAL NUCLEIC ACIDS AND ULTRAFILTRATION TO ISOLATE THE HYBRIDIZED MATERIAL

In order to test the efficacy of the hybridization and ultrafiltration method of the present invention, several tests were conducted. The tests were designed to show that retention of the probe nucleic acid by the ultrafiltration membrane depended on hybridization with target nucleic acid. The tests were done with three different types of probes: a single-stranded phage genome (used in the present example), an RNA transcript of a cloned sequence specific for Bacteroides target DNA (see EXAMPLE 2), and a copy DNA (cDNA) probe made by reverse transcription of bacterial ribosomal RNA (rRNA) (see EXAMPLE 3). The signal system most commonly used in these experiments is an enyzme catalyzed colorimetric reaction with the enzyme, horseradish peroxidase, covalently attached to the probe. However, also included are experiments in which the signal was an enzyme catalyzed colorimetric reaction in which the probe and the enzyme are both biotinylated and the enzyme is indirectly attached via a biotin-avidin-biotin linkage as well as experiments in which the probe was radioactive. In the first example the probe was a phage genome and the signal was an enzyme linked either directly or indirectly to the probe. Tests were conducted in accordance with the following sequence of steps:

A) Chromosomal DNA was isolated and purified from bacterial cells from *Bacillus subtilis* or *Escherichia coli* (both a laboratory strain and a fecal isolate) using standard procedures (Maniatis et al, *Molecular Cloning: A laboratory Manual*, Cold Spring Harbor Laboratory, New York, 1982). DNA purification was taken through phenol/chloroform extraction, ether extraction, and ethanol precipitation. The DNA was put into aqueous solution and analyzed quantitatively using spectrophotometry so that in all experiments the same quantity of DNA was used in control and experimental hybridizations.

B) A DNA probe was made that consisted of the entire M13mp18 bacterial virus (phage) genome. This single-stranded phage was chosen as a model probe because the genome is easy to isolate, and there are well worked out methods for cloning sequences into this phage (Heidecker et al., *A Versatile Primer for DNA Sequencing in the M13mp2 Cloning System*, Gene 10: 59–73, 1980; Hackett et al, *An Introduction to Recombinant DNA Techniques*, The Benjamin/Cummings Publishing Company, Inc., Menlo Park, Calif., 1984). Methods for easily using the inserted portion of such recombinant phage as a probe have been described (Brown et al., *Sensitive Detection of RNA Using Strand-Specific M13 Probes*, Gene 20: 139–144, 1982). Phage particles were grown and isolated and the DNA purified by phenol extraction as in DNA sequencing experiments (Hackett et al., *An Introduction to Recombinant DNA Techniques*, The Benjamin/Cummings Publishing Company, Inc., Menlo Park, Calif., 1984).

The probe was labelled by directly attaching the enzyme horseradish peroxidase (I.U.B.1.11.1.7) covalently using the protocol of Renz and Kurz, *A Colorimetric Method for DNA Hybridization*, Nucleic Acids Research 1.2: 3435–3444, 1984. This probe-enzyme complex was then used in a hybridization reaction with DNA from the bacterial nucleic acids as described below. The final concentration of the probe nucleic acid was 1.3 ug/ml in the final 380 ul hybridization solution. Hybridization was carried out in a microcentrifuge tube.

C) Chromosomal DNA was placed in an aqueous 0.75M phosphate buffer solution with a pH of 6.8, that was 50 percent formamide. The final concentration of the chromosomal DNA was 118 ug/ml in a total volume of 380 ul. The DNA was then melted into single strands by heating to 85° C. for four minutes. The DNA solution was cooled to 40° C. and labelled probe was added and hybridized at this temperature for three hours.

D) After completion of hybridization, the entire 380 ul hybridization mixture was loaded into an MPS-1 micropartition system, an apparatus for membrane ultrafiltration supplied by Areicon that uses a slow speed (clinical type) centrifuge. The MPS-1 contained an Amicon XM300 ultrafiltration membrane made of acrylic material which, by manufacturer's specifications, has a molecular weight cutoff of 300,000 daltons. The apparatus was centrifuged at low speed in a Damon Whisperfuge Model 1385 in a fixed angle rotor to near dryness. This speed is 2000 rpm and results in 500 RCF. The microcentrifuge tube was then washed with a 50 percent formamide, 0.75M phosphate buffer solution, with a pH of 6.8 that was prewarmed to 40° C. The wash was loaded into the same ultrafiltration membrane apparatus and again spun to near dryness. The filter was then washed twice more with the same solution, and then twice with a solution of 50 mM citrate buffer pH 4, warmed to 37° C. The second citrate buffer wash was allowed to stand on the membrane for 20 minutes at 37° C. prior to centrifugation in order to fully reactivate the peroxidase enzyme. One milliliter of a solution containing 67.5 ug/ml of 2,2'-azino-di-3ethylbenzthiazoline sulfonic acid and 0.006 percent $H_2O_2$ in 50 mM citrate buffer pH 4 was added to the apparatus. If peroxidase is present, it converts the substrate into a soluble blue dye. This solution was pipetted from the ultrafiltration membrane apparatus into 2 ml of citrate buffer in a spectrophotometric tube with a 1 cm path length and the optical density at $405_{nm}$ determined at various times.

The results are presented in TABLE I.

TABLE I

| Bacterial Source of Target DNA | OD* $405_{nm}$ after 45 Min. Peroxidase Reaction (Replicate Samples) |
| --- | --- |
| No target DNA added | 0.11, 0.11 |
| B. subtilis | 0.10, 0.20 |
| E. coli - fecal isolate | 0.55, 0.58 |
| E. coli - laboratory strain | 0.05, 0.05 |

*Optical density at an incident light of $405_{nm}$ wavelength using a Spec 20 spectrophotometer with a 1 cm path length is a measurement of color change due to enzyme activity.

The optical density values given in TABLE I above provide quantitative instrumental measurement of the extent of color change by virtue of enzymatic activity. Color is seen (as indicated by optical density at $^{405}$ nm of greater than a 0.1 to 0.2 background value) only if enzyme is present to catalyze a colorimetric reaction. The enzyme is covalently attached to the probe, so color is an indication that the probe is retained by the membrane. The probe is specific for *E. coli* fecal isolate DNA. The *B. subtilis* and *E. coli* laboratory strain DNA serve as negative controls in this experiment.

The data presented in TABLE I demonstrates that the retention of probe after hybridization by the ultrafiltration membrane depends on the presence of a specific target DNA (in this case, the fecal isolate form of *E. coli*). This specificity indicates that hybridization is responsible for probe retention by the filter.

In numerous analogous experiments, the control tube in which no target DNA was added to the hybridization reaction consistently yielded results similar to that provided by the tube containing the heterologous (*B. subtillis*) non-target DNA. Therefore, in some subsequent experiments the *B. subtillis* target nucleic acid tube served as a comparative example.

In a subsequent experiment, this probe showed the same specificity when crude lysates rather than purified bacterial DNA was used. To make crude lysates, the lysozyme, boiling water method of Maniatis et al, *Molecular Cloning: A laboratory Manual*, Cold Spring Harbor Laboratory, New York, 1980, was used. The debris from the lysis was pelleted and the supernatant used as a source of target nucleic acid. We also found that hybridization for 30 minutes was sufficient.

When the enzyme labelled M13mp18 probe was replaced with a biotinylated M13mp18 probe, it shows the same specificity as a probe that has the enzyme directly attached. The biotinylated enzyme was added after both hybridization and a stringent wash was completed. The tact that hybridized probe was retained even though it had no enzyme attached prior to washing indicates that retention by the ultrafiltration membrane does not appear to be due to some non-specific interaction between material in the target DNA preparation and the signal system enzyme.

EXAMPLE 2

HYBRIDIZATION OF PROBE RNA WITH VARIOUS BACTERIAL NUCLEIC ACIDS AND ULTRAFILTRATION TO ISOLATE THE HYBRIDIZED MATERIAL

This example was conducted to test the extent of probe retention by the filter membrane after hybridization using an RNA probe. Several tests were conducted in accordance with the following procedural steps:

A) Chromosomal DNA was isolated and purified from bacterial cells from *Bacillus subtilis*, *Bacteroides fragilis*, *Bacteroides thetaiotaomicron*, or *Escherichia coli* using standard procedures as in EXAMPLE 1 above.

B) An RNA probe was made by transcribing a Bacteroides-specific sequence that had been cloned into the cloning vector pGEMI right next to the T7 promoter. The vector was cut with the restriction endonuclease Hind III and the transcript made using T7 RNA polymerase. The transcript was labelled with the enzyme horseradish peroxidase (I.U.B.1.11.1.7) as in EXAMPLE 1. This probe-enzyme complex was then used in a hybridization reaction with DNA from the bacterial nucleic acids as described below. The final concentration of the probe nucleic acid was 2.6 ug/ml in the final 100 ul hybridization solution. Hybridization was carried out in a microcentrifuge tube.

C) Chromosomal DNA was placed in an aqueous 0.12M phosphate buffer solution with a pH of 6.8, that was 50 percent formamide. The final concentration of the chromosomal DNA was 200 ug/ml in a total volume of 100 ul. The DNA was then melted into single strands by heating to 85° C. for four minutes. The DNA solution was cooled to 47° C. and labelled probe was added and hybridized at this temperature for three hours.

D) After completion of hybridization, the entire 100 ul hybridization mixture was loaded into an MPS-1 apparatus containing an Amicon XM300 ultrafiltration membrane as in EXAMPLE 1. The apparatus was centrifuged at low speed as in EXAMPLE 1. The microcentrifuge tube was then washed as before but with 0.12M phosphate buffer solution prewarmed to 47° C. and then washed twice with a solution of 50 mM citrate buffer pH 4, as before. The dye was the same as used in EXAMPLE 1 and dye development was read in a Spec 20 as in EXAMPLE 1.

Following the above procedure, several replicate experiments using different probe and target DNA reagent preparations provided hybridization results as shown by the representative data give in TABLE II below.

TABLE II

| Bacterial Source of Target DNA | OD* 405 after 2 1/2 hour peroxidase reaction (replicate samples) |
| --- | --- |
| B. subtilis | 0.12, 0.10 |
| E. coli | 0.10, 0.10 |
| B. thetaiotaomicron | 0.35, 0.24 |
| B. fragilis | 0.58, 0.44 |

*Optical density at an incident light of 405$_{nm}$ wavelength using a Spec 20 spectrophotometer with 1 cm path length.

The optical density values given in TABLE II above provide quantitative instrumental measurement of the extent of color change by virtue of enzymatic acitivity. Color is seen (as indicated by optical density at $^{405}$ nm of greater than a 0.1 to 0.2 background value) only if enzyme is present to catalyze a colorimetric reaction. The enzyme is covalently attached to the probe, so color is an indication that the probe is retained by the membrane. The probe is specific for Bacteroides DNA. The *B. subtilis* and *E. coli* DNA serve as negative controls in this experiment. These data therefore show that the specificity of the hybridization reaction between the enzyme-labelled probe and the target DNA results in specific retention of probe by the filter.

In subsequent experiments, crude lysates were made of bacterial cultures using a lysozyme, boiling water method as in EXAMPLE 1 and shorter 30 minute hybridization incubation periods were used. Hybridization was still specific as shown in TABLE III below.

TABLE III

| | STRAIN | | |
| --- | --- | --- | --- |
| | B. fragilis | B. thetaiotaomicron | E. coli |
| OD$_{405}$ | 1.1 | 0.91 | 0.26 |

Readings are $^{OD}$405, indicating extent of enzyme catalyzed colorimetric reaction. Reaction time: 30 minutes.

These data show that neither lack of purification of the target DNA nor shorter hybridization time inhibited the binding of probe to the target, the retention of hybridized probe by the In another set of experiments designed to further test whether or not hybridization is responsible for retention of the probe by the ultrafiltration membrane, either the probe or the target nucleic acid (but not both) was exposed to nuclease. In the first such experiment, the RNA probe was incubated with 5 ug of Ribonuclease A for one hour at 37° C. prior to use as a probe. The results are presented in TABLE IV. In another such experiment, cell lysates were made in a buffer optimized for the activity of deoxyribonuclease I and treated the crude lysate with 10 units of a commercial preparation of this enzyme (certified to be RNase free) for one hour at 37° C. TABLE V shows the results of this experiment.

TABLE IV

RNase TREATMENT
B. fragilis

| Time of reaction in Min. | Tube #1, no RNase added | Tube #2, Probe RNase Treated |
|---|---|---|
| 5 | 0.68 | 0.14 |
| 10 | 0.90 | 0.18 |
| 15 | 1.00 | 0.21 |

TABLE V

DNase TREATMENT
B. fragilis

| Time of reaction in Min. | Tube #1, no DNase added | Tube #2, DNase added |
|---|---|---|
| 5 | 0.15 | 0.08 |
| 15 | 0.16 | 0.07 |
| 30 | 0.19 | 0.08 |
| 60 | 0.23 | 0.08 |
| 90 | 0.27 | 0.08 |
| 19 hr. | 0.75 | 0.11 |

Readings are $OD_{405}$, indicating extent of enzyme catalyzed colorimetric reaction. Hybridization time: 30 minutes.

These data (as presented in TABLES IV and V) indicate that nucleic acid hybridization causes probe retention by the ultrafiltration membrane since the destruction of either component of the hybridization mixture blocks filter retention of the probe.

EXAMPLE 3

HYBRIDIZATION OF PROBE cDNA WITH VARIOUS BACTERIAL NUCLEIC ACIDS AND ULTRAFILTRATION TO ISOLATE THE HYBRIDIZED MATERIAL

In this example, a copy DNA (cDNA) probe made by reverse transcription of bacterial ribosomal RNA (rRNA) was utilized. We purchased radioactive cDNA from Gen-Probe (Mycoplasma T. C. Detection Kit Catalog No. 1004 from Gen-Probe, San Diego, Calif.) and used this as probe in most experiments. Another probe was made using a procedure similar to that disclosed in Gen-Probe's patent application (Kohne, D. E., 1984, Patent Cooperation Treaty WO 84/02721) but labelled with an enzyme rather than with radioactive label. Briefly, the Gen-Probe procedure uses purified rRNA as a template for the synthesis of cDNA using reverse transcriptase. The Gen-Probe kit contains cDNA made from Mycoplasma rRNA. The enzyme labelled probe was fabricated using 1400 units of cloned Moloney Murine Leukemia Virus reverse transcriptase (Catalog #8025SA) purchased from Bethesda Research Laboratories per 7 ug of B. subtilis rRNA. The specificity of both probes seems similar, they bind to target rRNA of all prokaryotic species tested.

These experiments allowed a comparison between the filter retention method of separation with hydroxylapatite separation employed by the Gen-Probe Mycoplasma T. C. detection kit. The single-stranded cDNA probe has homology with all prokaryotic ribosomal sequences tested, we used B. subtilis crude lysates as a source of rRNA target nucleic acid. The probe contains tritium-labelled nucleotides and detection uses a scintillaton counter. TABLE VI shows data from side-by-side comparison of the two methods. Hybridization followed the detection kit label instructions and was carried out in purely aqueous solution at 72° C. The only difference between these two was in separation of hybridized from unhybridized probe. The ultrafiltration membrane used in these experiments was an Areicon YM100, a cellulosic membrane having a MWCO of 100,000. All data is given in counts per minute. Duplicate lysate samples were made. Positive and negative controls were provided in the kit. It was noted that the positive control failed to develop a signal with the filter separation method.

TABLE VI

Ultrafiltration on a Cellulosic Membrane With an MWCO of 100,000 Versus Hydroxylapatite Method Using a Radioactive-Labelled Probe With a Nucleic Acid Target Consisting of B. subtilis Crude Lysate

| | Separation Method | | | | | | | |
|---|---|---|---|---|---|---|---|---|
| | Ultrafiltration | | | | Hydroxylapatite | | | |
| | Sterile Media | Positive Control | Negative Control | Lysate | Sterile Media | Positive Control | Negative Control | Lysate |
| CPM* | 137 | 202 | 44 | 2644 2456 | 230 | 2308 | 348 | 544 1089 |

Total Counts Added: 6170
Background: 20
*Counts per minute of radioactivity.

The data presented in TABLE VI demonstrate the utility of ultrafiltration membrane separation of hybridized from unhybridized probe using a very different probe, as well as its utility with a probe labelled with radioactivity.

In another set of experiments, various membrane filters were tested and compared using this radioactive cDNA probe. In this experiment we used an XM 300 membrane (used in the first and second example with enzyme-labelled probe) and a polysulfone membrane supplied by Schleicher & Schuell with an MWCO of 1,000,000. TABLE VII shows the results of this experiment. Data is shown in counts per minutes. The target nucleic acid is B. subtilis crude lysate.

TABLE VII

| Filter Membrane Type | Membrane Pore Size | Lysate | CPM* Retained |
|---|---|---|---|
| acrylic | 300,000 MWCO | none | 233 |
| acrylic | 300,000 MWCO | present | 6,325 |
| polysulfone | 1,000,000 MWCO | none | 24 |
| polysulfone | 1,000,000 MWCO | present | 4,184 |

Total counts added: 13,316
*Counts per minute.

These data, when combined with the data from TABLE VI, show that membranes of cellulosic, acrylic, or polysulfone construction and with MWCO ranges of from 100,000 to 1,000,000 can be used to separate hybridized from unhybridized nucleic acid.

In another set of experiments, a cDNA probe with an enzyme-labelled signal system was tested with the ultrafiltration system of the present invention. In the same experiment a hybridization competition between the probe cDNA probe and an unlabelled cDNA reduces the amount of probe retained by the filter. The presence of nucleic acid of the same sequence as the probe should reduce the signal and therefore the amount of probe retained by the filter if hybridization of probe to target rRNA is causing probe retention by the filter. The unlabelled nucleic acid competes with the probe for hybridization sites on the target nucleic acid. In this experiment 10 ug of purified rRNA was used as the target and the probe consisted of 0.42 ug of enzyme-labelled cDNA. The 10 ug of competitive cDNA was from the same preparation as the probe, but no enzyme had been attached to it. The probe and competitive cDNA were added simultaneously to the target rRNA. Hybridizations were carried out in accordance with the procedure described in EXAMPLE 2. The results are presented in TABLE VIII. Results are in $OD_{405}$ after 20 minutes of peroxidase reaction using a hybridization time of 30 minutes.

TABLE VIII

| Target rRNA | Competitive cDNA | $OD^*_{405}$ |
|---|---|---|
| − | − | 0.13 |
| + | − | 0.99 |
| + | + | 0.32 |

*Optical density at an incident light of $405_{nm}$ wavelength using a Spec 20 spectrophotometer with a 1 cm path length is a measurement of color change due to enzyme activity.
+ denotes additive is present.
− denotes additive is absent.

This experiment demonstrates that the ultrafiltration method servesto separate hybridized from unhybridized probe of a variety of types, labelled with both enzymes and radioactivity. It also adds more data to support the hypothesis that hybridization is indeed the most likely explanation for retention of probe by the filter since competition with an unlabelled probe significantly reduced the measured $OD_{405}$ from 0.99 (without competitive cDNA) down to 0.32 (with competitive cDNA).

What is claimed is:

1. A kit for effecting separation of labelled probe nucleic acid molecules from hybridized probe/target nucleic acid molecules consisting essentially of:

(a) a sample of labelled probe nucleic acid molecules and (b) a membrane filter having a pore size within a range such that unhybridized labelled probe nucleic acid molecules pass through said membrane filter whereas labelled probe nucleic acid molecules hybridized with complementary target nucleic acid molecules are retained on said membrane filter, said pore size provided a molecular weight cutoff of between 200,000 and about 300,000 Daltons, wherein said labelled probe nucleic acid molecules have an enzyme label, either covalently attached to the probe or indirectly attached to the probe by means of a biotin-avidin-biotin linkage, and wherein said kit additionally contains an enzyme substrate to assist in identification of hybridized probe/target nucleic acid molecules.

2. The kit of claim 1 which additionally contains a buffer solution for said enzyme to assist in identification of hybridized probe/target nucleic acid molecules.

* * * * *